United States Patent [19]

Kutscher et al.

[11] Patent Number: 5,539,107
[45] Date of Patent: Jul. 23, 1996

[54] METHOD FOR THE PRODUCTION OF AZAPHENOTHIAZINES

[75] Inventors: Bernhard Kutscher, Maintal; Hans-Reinhold Dieter, Darmstadt, both of Germany

[73] Assignee: ASTA Medica Aktiengesellschaft, Frankfurt am Main, Germany

[21] Appl. No.: 423,049

[22] Filed: Apr. 17, 1995

Related U.S. Application Data

[60] Division of Ser. No. 208,120, Mar. 9, 1994, which is a continuation-in-part of Ser. No. 198,056, Feb. 18, 1994, abandoned.

[30] Foreign Application Priority Data

Feb. 19, 1993 [DE] Germany .................. 43 05 080.8

[51] Int. Cl.⁶ .................. C07D 513/04; C07D 401/12
[52] U.S. Cl. .................. 544/14; 544/34; 546/264; 546/312
[58] Field of Search .................. 544/14, 34; 546/312, 546/264, 255

[56] References Cited

U.S. PATENT DOCUMENTS 3,010,961  11/1928  Schindler .................. 260/243

OTHER PUBLICATIONS

Maki, Y. Rearrangement Reaction. XI. Smiles Re-arrangement on Pyridine Derrivatives. Journal of the Pharmaceutical Society of Japan. vol. 86, pp. 50–54 (1966).

*Primary Examiner*—Mukund J. Shah
*Assistant Examiner*—Anthony P. Bottino
*Attorney, Agent, or Firm*—Cushman Darby & Cushman

[57] ABSTRACT

A process for the production of azophenothiazine derivatives having either of the following structures:

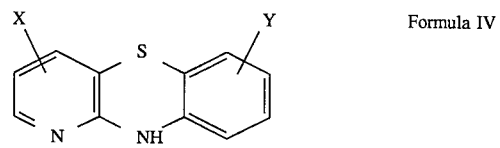

Formula IV

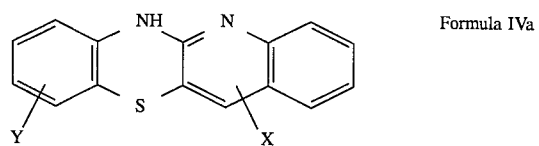

Formula IVa where X and Y include alkyl, alkoxy, halogen, hydrogen, carboxy, or carboxy alkyl substituents. These compounds are precursors to pharmaceutically active compounds such as pipacetate. The process involves the reaction of a 2-chloropyridine with a 2-mercaptoaniline or a dimer of 2-(2-mercaptophenylamino)pyridine in an inert solvent, e.g., ∇-methylpyrolidone in the presence of an oxidizing agent, e.g., performic acid.

5 Claims, No Drawings

METHOD FOR THE PRODUCTION OF AZAPHENOTHIAZINES

This is a division of application Ser. No. 08/208,120, filed Mar. 9, 1994 which is a Continuation-In-Part of Ser. No. 08/198,056, filed Feb. 18, 1994, abandoned.

The present invention relates to a novel, improved method for the production of azaphenothiazines, preferably pyrido(3,2-b) benzothiazines and their salts, and to certain novel compounds.

BACKGROUND OF THE INVENTION

Azaphenothiazine is a valuable precursor for pharmaceutically active substances such as pipacetate (INN) Selvigon®, Isothipendyl (INN) (Andantol®) and prothipendyl (INN) (Dominal®). The synthesis of the compound is described in German Patent DE-PS 964050 as well as in J. Org. Chem. 25, pp. 1156–1157 (1959). The synthesis starts with 2-phenylaminopyridine and elementary sulfur and proceeds by means of cyclization in the melt, using iodine catalysis. The process has several disadvantages: a mole of $H_2S$ is formed as a by-product; a high reaction temperatures of 230° C.–250° C. is necessary, in contrast to benzothiazines (phenothiazines); the workup procedure is expensive. The sulfonation reagents $SCl_2$ and $S_2Cl_2$ used, under rather mild conditions in the process described in the German patent leads to unsatisfactory yields when the process is repeated.

In addition to this one-stage method starting from 2-phenylaminopyridine, multi-stage methods are known from the work of H. L. Yale and E. Sowinski, J. Org. Chem., p. 1651 (1958) and French Patent Application FR No. 1,170,119 which methods start either from 2-chloro-3-aminopyridine or 2-chloro-3-nitropyridine and 2-aminothiophenol (2-mercaptoaniline) (the so-called Smiles rearrangement cf. N. L. Smiles, J., Org. Chem. 15, 1125 (1950) and R. R. Gystra (Ed.) Phenothiazines and 1,4-benzothiazines—Chemical and Biomedical Aspects, Elsevier, Amsterdam 1988), (U.S. Pat. No. 2,943,086) or 2-chloro-3-mercaptopyridine and 2-chloro-nitrobenzene. Both methods were incapable of being scaled up to an industrial process for economic reasons.

In all the methods cited, the target compound is purified as a base using vacuum distillation, and then by salt formation.

This purification method stresses the product thermally and results in residues which must be disposed of as special waste, because they can not be re-utilized. Purification via salt formation requires a further additional method step and raises the expense.

There is, therefore, a need for a method which avoids the described disadvantages of the state of the art and which, moreover, meets the requirements placed on the environmental compatibility of production methods, which requirements have increased since those methods were developed, by avoiding byproducts and high reaction temperatures. In addition, it is advantageous to save a few method steps.

SUMMARY OF THE INVENTION

In accordance with the present invention, it has been found surprisingly that a better process can be achieved for the conversion of 2-chloro-pyridines of the General Formula I:

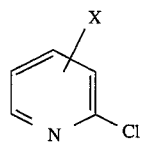

Formula I in which:

X signifies hydrogen, alkyl groups with a chain length of 1–6 carbon atoms such as e.g. the methyl group, the ethyl group, the propyl group, the isopropyl group, the butyl group, the isobutyl group and the tert.-butyl group, halogen substituted alkyl groups, preferably with 1–6 carbon atoms, substituted by one or more halogen atoms, halogen, such as e.g. fluorine, chlorine and bromine, alkoxy with 1–5 carbon atoms, carboxy and carboxy alkyl with 1–5 carbon atoms. There can be one or more of these groups in the 4, 5 or 6 positions of the 2-chloro-pyridine structure. This material is reacted with a 2-mercaptoaniline of the General Formula II

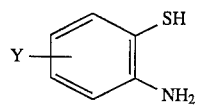

Formula II in which:

Y signifies hydrogen, alkyl groups with a chain length of 1–6 carbon atoms such as e.g. the methyl group and the ethyl group, the propyl group, the isopropyl group, the butyl group, the isobutyl group and the tert.-butyl group, alkyl groups, preferably with 1–6 carbon atoms, substituted by one or more halogen atoms, halogens such as e.g. fluorine, chlorine and bromine, alkoxy with 1–5 carbon atoms, carboxy and carboxy alkyl with 1–5 carbon atoms. There can be one or more of these groups in the 4, 5 or 6 positions of the 2-mercaptoaniline structure.

Alternatively, the 2-chloropyridine of General Formula I is reacted with disulfides of the General Formula III:

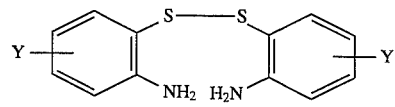

Formula III in which Y has the same meanings as mentioned above in connection with General Formula II.

The reaction is carried out in the presence of catalytic or stoichiometric amounts of suitable oxidizing agents, e.g. per acids, especially performic acid, peracetic acid or perbenzoic acid, $H_2O_2$, $Fe^{3+}$ salts, V/Mo/Ag oxides, peroxides, $Th(OCOCF_3)_3$, molecular oxygen, preferably iodine—either without solvent or with an inert, high-boiling solvent or in the presence of a free radical initiator such as azabisbutyronitrile, di-tert.-butylperoxide or benzolyperoxide.

The following can be considered as inert, high-boiling solvents useful for the process: ∇-methylpyrrolidone, sulfolane, diphenylether, diphenyl, dimethyl formamide, dimethyl acetamide, and diphyl (25% diphenyl/75% diphenyl ether). The temperature is approximately 150° C.–210° C., preferably 190° C.–200° C. The isolation of 2-mercaptophenylaminopyridine intermediate stage is possible but not absolutely necessary. Scheme I

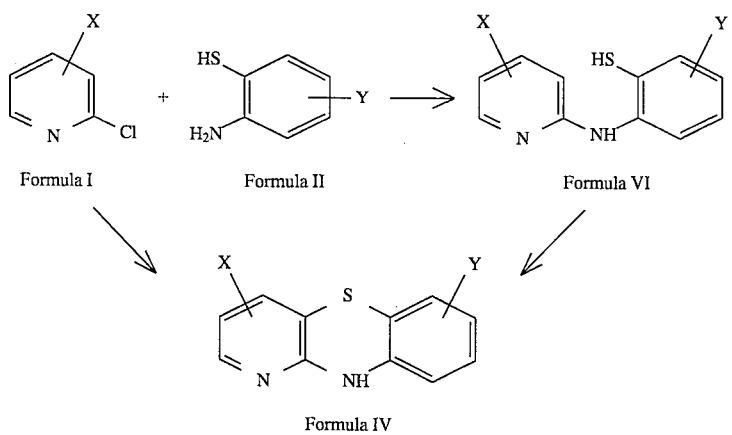

Formula I   Formula II   Formula VI

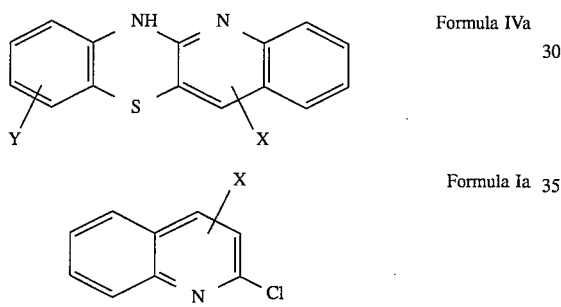

Formula IV

The compounds with the General Formula VI, in which the meanings of groups X and Y are the same as above, can be isolated or they can be converted further, without isolation, to compounds of general formula IV, in which, again, the meanings of the groups X and Y is the same as above.

Novel 6-aza-benzo[b]phenothiazine derivatives, of Formula IVa, are obtainable according to the same process, starting with 2-quinoline derivatives of Formula Ia.

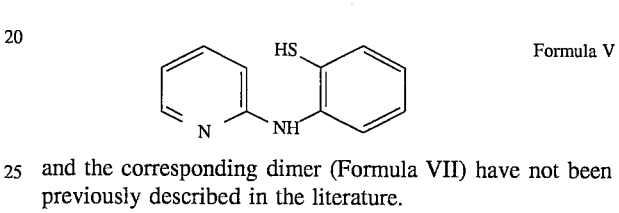

Formula IVa

Formula Ia

Another feature of the method is that the corresponding azaphenothiazinium salts can be directly crystallized in very good quality by simply transferring the reaction mixture into dilute aqueous acids, e.g. mineral acids, preferably dilute hydrochloric acid; the liberation of the azaphenothiazines from their salts can be carried out in a conventional manner by treatment with a base. Bases which can be used are e.g. alkali hydroxides; it is preferable if dilute NaOH or concentrated ammonia is used.

Further advantages of the method are:

1. Distinctly shortened reaction times
2. The addition of the nickel catalysts and iron catalysts required according to German patent DE-PS 964050 can be eliminated. These iron or nickel catalysts contribute contamination to waste water which is avoided by the method of the invention.

DETAILED DESCRIPTION OF PREFERRED EMBODIMENTS

Various embodiments of the novel method of the invention are illustrated in the following examples. The compound 2-(2-mercaptophenylaminopyridine) (MAP), see Example 2 (Formula V), isolated as an intermediate or generated directly in situ and converted further

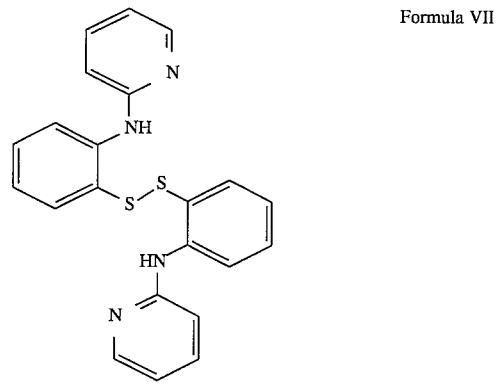

Formula V and the corresponding dimer (Formula VII) have not been previously described in the literature.

Formula VII

The following flow chart clarifies once again the reaction of the invention byway of example.[1]

[1] abbreviations: AP: azaphenothiazine SH-PAP: 2-(2-mercaptophenylamino) pyridine

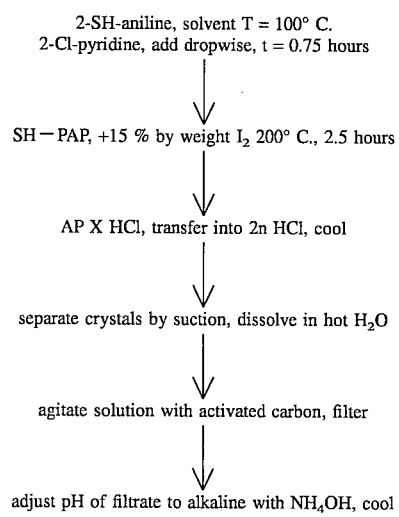

Flow chart: Azaphenothiazine ("one-pot" method)

2-SH-aniline, solvent T = 100° C.
2-Cl-pyridine, add dropwise, t = 0.75 hours

↓

SH–PAP, +15 % by weight $I_2$ 200° C., 2.5 hours

↓

AP X HCl, transfer into 2n HCl, cool

↓ separate crystals by suction, dissolve in hot $H_2O$

↓ agitate solution with activated carbon, filter

↓ adjust pH of filtrate to alkaline with $NH_4OH$, cool

-continued
Flow chart: Azaphenothiazine ("one-pot" method)

↓ remove AP base by suction, dry

EXAMPLE 1

Synthesis of azaphenothiazine (AP) 0.4 mole 2-mercaptoaniline (MW=125.2) is added to 80 ml diphyl (25% diphenyl/ 75% diphenyl ether) and 0.4 mole 2-chloropyridine (MW= 113.6) is added dropwise at 90° C.–125° C. This causes an exothermic transition from suspension to emulsion to takes place. Then, 0.11 equivalents (14.3 g=15% by weight relative to converted 2-mercaptoaniline) of iodine are added, the reaction mixture is agitated 3 hours at 200° C., and then it is cooled to 100° C., 200 ml 2 nHCl are added and the phases are separated. The upper layer (diphyl) is separated off and can be reused after drying with $Na_2SO_4$. Azaphenothiazine hydrochloride crystallizes out of the lower aqueous layer after the cooling off. The product is removed by suction, dissolved in 300 ml $H_2O$ and agitated with 10 g activated carbon. After the activated carbon has been filtered off, the pH filtrate is adjusted with 25% NaOH (pH 9–11). The precipitating AP base is removed by suction and dried at 60° C.

AP base yield: 30.4 g (58%) melting point: 114°–116° C.

Elemental analysis: C calc. 65.97 obs. 66.2 H calc. 4.03 obs. 3.96 N calc. 13.99 obs. 13.92

EXAMPLE 2

Synthesis of 2-(2-mercaptophenylamino) pyridine (MAP)

340.5 g (3 moles) 2-chloropyridine are added dropwise to a boiling solution of 375 g (3 moles) 2-mercaptoaniline in 1.8 liters 2-propanol with agitation and under an atmosphere of protective gas within 15 min. After termination of the addition, the mixture is agitated for 5 hours at boiling temperature. The mixture is then allowed to cool to room temperature, and the precipitated yellowish product is filtered off and washed twice with 50 ml 2-propanol per wash. After drying in a vacuum, 592 g (86% of theory), 2-(2-mercapto-phenylamino) pyridine is obtained as colorless to yellowish crystals.

Melting interval 152° C.–162° C.

Elemental analysis: Calc.: C: 55.34 H: 4,64 N: 11.73 Obs.: C: 55.60 H: 4.69 N: 11.72

EXAMPLE 3

Synthesis of azaphenothiazine (pyrido-[3,2-b][1,4]-benzothiazine=AP)

Variant A

A suspension consisting of 50 g 2-(2-mercaptophenylamino)pyridine, 8 g iodine and 200 ml sulfolane is heated with agitation for 3 hours to 200° C. The sulfolane is then distilled off in a vacuum. The residue is mixed with 150 ml n-butanol and, after the addition of 100 ml 10% sodium hydroxide solution, agitated 1 hour at 80° C. After the mixture has cooled off, the alcoholic phase is separated and evaporated to low bulk in a vacuum. The residue is taken up in 100 ml 2N hydrochloric acid and intensively agitated after the addition of 5 g activated carbon for 1 hour at 90° C.–95° C. Then, insoluble components are filtered off and the thiopyram hydrochloride allowed to crystallize with agitation at 0° C.–5° C. The orange-yellow crystals are filtered off and washed twice with 20 ml water per wash. The product is then mixed with 50 ml water. 15 ml concentrated ammonia is added drop-by-drop to the resulting mixture at 80° C.–85° C. After the dropwise addition is completed, the mixture is allowed to cool to room temperature and is agitated for 30 min. The precipitated thiopyram base is removed by suction, washed twice with 10 ml water per wash and dried in a vacuum. 17.7 g (42% of theory) thiopyram (=AP) are obtained.

Melting point: 115° C.–116° C.

Elemental analysis: Calc.: C: 65.97 H: 4.03 N: 13.99 Obs.: C: 65.43 H: 4.03 N: 13.96

Variant B

A suspension of 50 g 2-(2-mercaptophenylamino)pyridine, 7,5 g iodine and 100 ml diphyl is heated with agitation 2.5 hours to 200° C.–205° C. After having cooled off to 80° C. the reaction mixture is mixed with 100 ml 2N hydrochloric acid and agitated 15 min at 80° C.–85° C. Then the phases are separated. After cooling off, thiopyram hydrochloride crystallizes out of the aqueous layer. The orange-yellow crystals are filtered off and washed twice with 20 ml water per wash. 15 ml concentrated ammonia is added drop-by-drop to the resulting mixture at 80 C.–85° C. After the dropwise addition is competed, the mixture is allowed to cool to room temperature and is agitated for 30 minutes. The precipitated thiopyram base is removed by suction, washed twice with 10 ml water per wash and dried in a vacuum. 18.9 g AP base (45.1% of theory) are obtained.

Melting point: 114° C.–116° C.

Elemental analysis: Calc.: C: 65.97 H: 4.03 N: 13.99 Obs.: C: 65.27 H: 4.02 N: 13.93

Variant C

A mixture of 50 g 2-(2-mercaptophenylamino)-pyridine and 7.5 g iodine are heated with agitation for 2 hours to 200° C.–205° C. After having cooled off, the melt is mixed with 30 ml 10% hydrochloric acid and 5 g activated carbon and agitated for 1 hour at approximately 70° C. Then, insoluble components are filtered off and the thiopyram hydrochloride is allowed to crystallize with agitation at 0° C.–5° C. The orange-yellow crystals are filtered off and washed twice with 10 ml water per wash and dried in a vacuum. 14.5 g (34.7% of theory) AP are obtained.

Melting point 106° C.–110° C.

Elemental analysis: Calc.: C: 65.97 H: 4.03 N: 13.99 Obs.: C: 66.06 H: 4.13 N: 14.24

Variant D 28.4 g 2-chloropyridine are added drop-by-drop to a boiling solution of 31.3 g 2-mercaptoaniline in 150 ml 2-propanol with agitation and under an atmosphere of protective gas within 15 minutes. After the addition is completed, the mixture is agitated 7 hours at boiling temperature. The isopropanol is then distilled off. 9 g iodine are added to the residue and the mixture heated 1.5 hours at 200° C.–205° C. with agitation. The melt is combined with 150 ml butanol and agitated, after the addition of 100 ml 10% sodium hydroxide solution, for 1 hour at 80° C. After having cooled off, the alcoholic phase is separated off and evaporated to low bulk in a vacuum. The residue is taken up in 100 ml 2N hydrochloric acid and intensively agitated, after the addition of 5 g activated carbon, for 1 hour at 90° C.–95° C. Then, insoluble components are filtered off and the thiopyram hydrochloride is allowed to crystallize with agitation at 0° C.–5° C. The orange-yellow crystals are filtered off and washed twice with 20 ml water per wash. The product is then mixed with 150 ml water. 15 ml concentrated ammonia is added drop-by-drop to the resulting mixture at 80° C.–85° C. After the dropwise addition is completed, the mixture is allowed to cool to room temperature and is agitated for 30 minutes. The precipitated thiopyram base is removed by suction, washed twice with 10 ml water per time and dried in a vacuum. 8.9 g (38% of theory) thiopyram are obtained.
Melting point: 115° C.–116° C.
Elemental analysis: Calc.: C: 65.97 H: 4.03 N: 13.99 Obs.: C: 65.89 H: 4.04 N: 14.09

The compounds according to Examples 4–6 were obtained according to the procedure in Example 1 using the suitable precursors.

EXAMPLE 4

1-aza-8-trifluoromethyl-phenothiazine hydrochloride
Molecular weight: 304.63
Melting point: 234° C.
Elemental analysis: Calc.: C: 47.30 H: 2.65 N: 9.19 Obs.: C: 47.05 H: 2.48 N: 8.79

EXAMPLE 5

1 aza-2-methylphenothiazine
Molecular weight 305.13
Melting point: 186° C.
Elemental analysis: Calc.: C: 47.23 H: 4.62 N: 9.18 Obs.: C: 47.28 H: 3.62 N: 9.21

EXAMPLE 6

1-aza-3-carboxy-phenothiazine (D 22571)
Molecular weight 224.18
Melting point: >300° C.
Elemental analysis: Calc.: C: 59.00 H: 3.30 N: 11.47 Obs.: C: 57.85 H: 3.23 N: 11.07

EXAMPLE 7

6-aza-benzo[b]phenothiazine (D 22646)
Starting with 2-chloroquinoline according to the method of Example 1.
Since an aqueous workup with dilute HCl is not possible, diphenyl is separated by decantation from the solvent and the solid residue recrystallized from ethanol.
Molecular weight: 286.78
Yield: 48%
Melting point: 240°–245° C.
Elemental analysis: Calc.: C: 62.82 H: 3.87 N: 9.77 Obs.: C: 62.75 H: 3.88 N: 9.70

EXAMPLE 8

6-aza-5-(2-dimethylaminopropyl)benzo[b]thiazine hydrochloride
0.02 mole (5 g) 6-aza-benzo[b]phenothiazine (Example 7) is heated in 30 ml toluene with 4 g potassium hydroxide and 1 ml TDA-1 and then 0.02 mole (3.2 g) dimethylaminopropyl chloride HCl is added. After 2 hours reflux the mixture is concentrated by evaporation and the orange-colored oil obtained is crystallized from isopropanolic hydrochloric acid.
Yield: 3 g (39%)
Melting point: 185° C.
Elemental analysis: Calc.: C: 56.34 H: 5.91 N: 9.85 Obs.: C: 56.60 H: 5.86 N: 9.84

EXAMPLE 9

The method was analogous to Example 8, using trichloroethylchloroformate.
Melting point: 185° C.
Elemental analysis: Calc.: C: 50.78 H: 2.60 N: 6.58 Obs.: C: 50.54 H: 2.53 N: 6.44

EXAMPLE 10

The method was analogous to Example 8, using N-chloromethyl-N[2-methoxyphenyl]piperazine
Melting point: 234° C.
Elemental analysis Calc.: C: 66.58 H: 5.79 N: 11.09 Obs.: C: -H: 5.73 N: 10.91

| | R | Yeild | Melting Point |
|---|---|---|---|
| Example 11 | —CH$_2$—C$_6$H$_2$(OCH$_3$)$_3$ | | |
| Example 12 | —(CH$_2$)$_3$—N(CH$_3$)$_2$ with pyridyl-CH$_3$ | 52% | 96° C. |
| Example 13 | —CO$_2$CH$_2$CH$_2$O—CH(N-pyridyl)—CH$_3$ | 44% | 221° C. |
| Example 14 | —(CH$_2$)$_3$—N(piperazinyl)-phenyl | | |

The compounds according to Examples 11–14 were obtained by a method analogous to Example 8. Group R is located on the phenothiazine nitrogen.

What is claimed is:
1. A method of producing an azaphenothiazine of Formula IV or Formula IVa

Formula IV

Formula IVa in which X signifies at least one member of the group consisting of hydrogen, alkyl groups with a chain length of 1–6 carbon atoms, halogen substituted alkyl groups substituted by at least one one halogen atom, halogen, alkoxy with 1–5 carbon atoms, carboxy and carboxy alkyl with 1–5 carbon atoms and in which Y signifies hydrogen, alkyl groups with a chain length of 1–6 carbon atoms, alkyl groups substituted by at least one halogen atom, halogens, alkoxy with 1–5 carbon atoms, carboxy and carboxy alkyl with 1–5 carbon atoms said method comprising reacting a compound of Formula I or Formula Ia

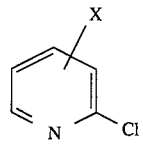

Formula I

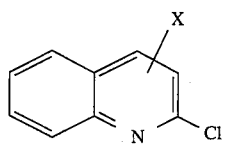

Formula Ia in which X has the meaning given above, with a compound of Formula II or Formula III

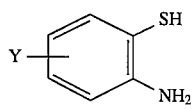

Formula II

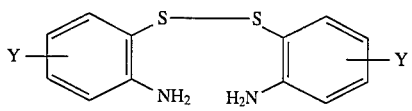

Formula III in which Y has the meaning given above, in the presence of an oxidizing agent in an inert solvent.

2. A method according to claim 1 in which a member of the group consisting of iodine, iron(III) salts, $MnO_2$, peroxides, peracids, $H_2O_2$, V/Mo/Ag oxides, molecular oxygen and free radical initiators is used as the oxidizing agent.

3. The dimer of 2-(2-mercaptophenylamino)pyridine.

4. The method according to claim 1, wherein the inert solvent is a high-boiling solvent selected from the group consisting of $\nabla$-methylpyrrolidone, sulfolane, diphenylether, diphenyl, dimethyl formamide, dimethyl acetamide, and diphyl (25% diphenyl/75% diphenyl ether).

5. The method according to claim 1, wherein the method is a one pot method.

* * * * *